US009669165B2

(12) United States Patent
Mackey et al.

(10) Patent No.: US 9,669,165 B2
(45) Date of Patent: Jun. 6, 2017

(54) SYRINGE WITH TWO-STAGE SEALING PRESSURE

(71) Applicant: AbbVie Inc., North Chicago, IL (US)

(72) Inventors: Sean E. Mackey, Grayslake, IL (US); Ji Zhou, Grayslake, IL (US); Martin J. Gibler, West Chester, OH (US); Dennis Y. Lee, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 108 days.

(21) Appl. No.: 13/829,251

(22) Filed: Mar. 14, 2013

(65) Prior Publication Data
US 2014/0228802 A1 Aug. 14, 2014

Related U.S. Application Data

(60) Provisional application No. 61/763,777, filed on Feb. 12, 2013.

(51) Int. Cl.
A61M 5/14 (2006.01)
A61M 5/315 (2006.01)
(Continued)

(52) U.S. Cl.
CPC .... A61M 5/31505 (2013.01); A61M 5/14546 (2013.01); A61M 5/31501 (2013.01);
(Continued)

(58) Field of Classification Search
CPC ............ A61M 5/31505; A61M 5/3135; A61M 5/2448; A61M 5/2066; A61M 5/19;
(Continued)

(56) References Cited

U.S. PATENT DOCUMENTS 4,439,184 A * 3/1984 Wheeler ............... A61M 3/005
604/191
5,338,309 A * 8/1994 Imbert ............... A61M 5/3135
604/110
(Continued)

FOREIGN PATENT DOCUMENTS

EP 0511402 A1 11/1992
EP 0960616 A2 12/1999
(Continued)

OTHER PUBLICATIONS

International Search Report and Written Opinion for Application No. PCT/US2013/031750, mailed on May 21, 2014, 22 pages.
(Continued)

Primary Examiner — Laura Bouchelle
Assistant Examiner — Justin L Zamory
(74) Attorney, Agent, or Firm — McCarter & English, LLP; David R. Burns

(57) ABSTRACT

A syringe includes a barrel, a plunger, and a sealing member creating a seal between the plunger and the barrel. The barrel includes a first portion with a first inner diameter and a second portion with a second inner diameter that is larger than the first inner diameter. The sealing member engages the first portion of the barrel to give rise to a first contact pressure when the barrel is filled with product. The first contact pressure is sufficient to maintain a gas-tight seal over the expected temperature ranges −25° C. to 40° C. A first force is applied to the plunger to overcome the first contact pressure and move the plunger out of the first portion and into the second portion to dispense product. The sealing member engages the second portion of the barrel to give rise to a second contact pressure that is lower than the first contact pressure. A second force lower than the first force is sufficient to overcome the second contact pressure and move the plunger in the second portion to continue dispensing
(Continued)

product. The syringe may include a restraining element for accommodating expansion of the product during freezing.

8 Claims, 15 Drawing Sheets

(51) Int. Cl.
*A61M 5/145* (2006.01)
*A61M 5/31* (2006.01)
*A61J 7/00* (2006.01)
*A61J 15/00* (2006.01)
*A61M 5/00* (2006.01)

(52) U.S. Cl.
CPC ........ *A61M 5/31513* (2013.01); *A61J 7/0053* (2013.01); *A61J 15/0015* (2013.01); *A61J 15/0061* (2013.01); *A61J 15/0069* (2013.01); *A61J 15/0076* (2015.05); *A61M 5/002* (2013.01); *A61M 5/3135* (2013.01); *A61M 2005/3101* (2013.01); *A61M 2005/3106* (2013.01); *A61M 2005/3131* (2013.01); *A61M 2005/31506* (2013.01)

(58) Field of Classification Search
CPC .............. A61M 5/31501; A61M 5/284; A61M 5/31596; A61M 5/31513; A61M 2005/1786; A61M 2005/3131; A61M 2005/3114
See application file for complete search history.

(56) References Cited

U.S. PATENT DOCUMENTS

| 5,435,076 | A | * | 7/1995 | Hjertman | A61M 5/284 |
| | | | | | 206/219 |
| 5,637,100 | A | * | 6/1997 | Sudo | A61M 5/284 |
| | | | | | 604/218 |
| 8,096,971 | B2 | * | 1/2012 | Bassarab | A61M 5/2448 |
| | | | | | 604/84 |
| 2001/0041867 | A1 | * | 11/2001 | Schottli | A61M 5/5066 |
| | | | | | 604/110 |
| 2003/0212368 | A1 | | 11/2003 | Shue et al. | |
| 2004/0054332 | A1 | | 3/2004 | Ferguson | |
| 2004/0141886 | A1 | | 7/2004 | Py et al. | |
| 2005/0148932 | A1 | | 7/2005 | Rimlinger et al. | |
| 2009/0326458 | A1 | * | 12/2009 | Chong | A61B 5/14532 |
| | | | | | 604/152 |
| 2010/0022990 | A1 | * | 1/2010 | Karpowicz | A61M 1/0088 |
| | | | | | 604/543 |

FOREIGN PATENT DOCUMENTS

| EP | 1488818 A1 | 12/2004 |
| WO | 01/23017 | 4/2001 |
| WO | 0230494 A2 | 4/2002 |
| WO | 2006056452 A1 | 6/2006 |
| WO | 2007005902 A2 | 1/2007 |

OTHER PUBLICATIONS

Partial International Search Report for Application No. PCT/US2013/031750 mailed Jan. 7, 2014, 7 pages.

* cited by examiner

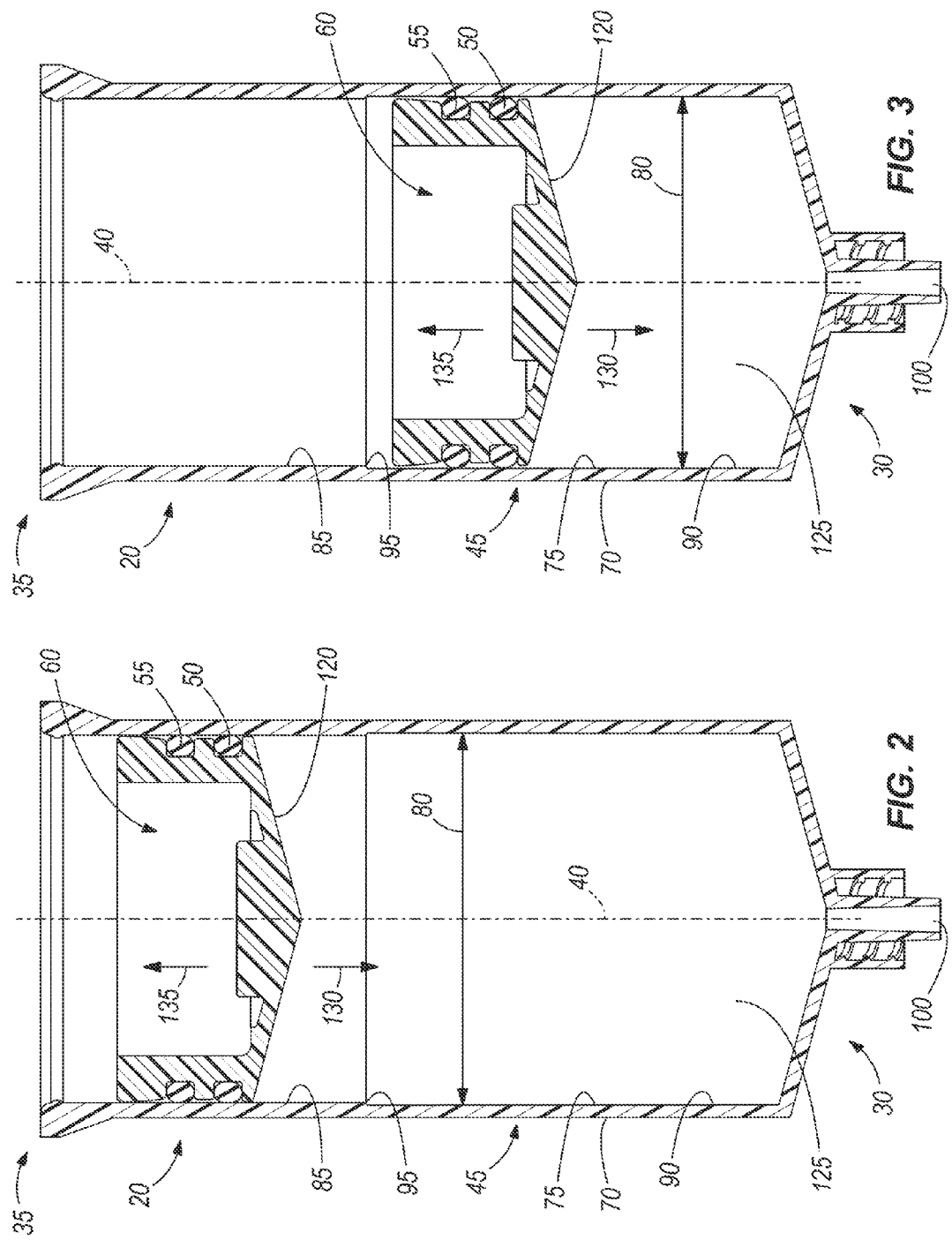

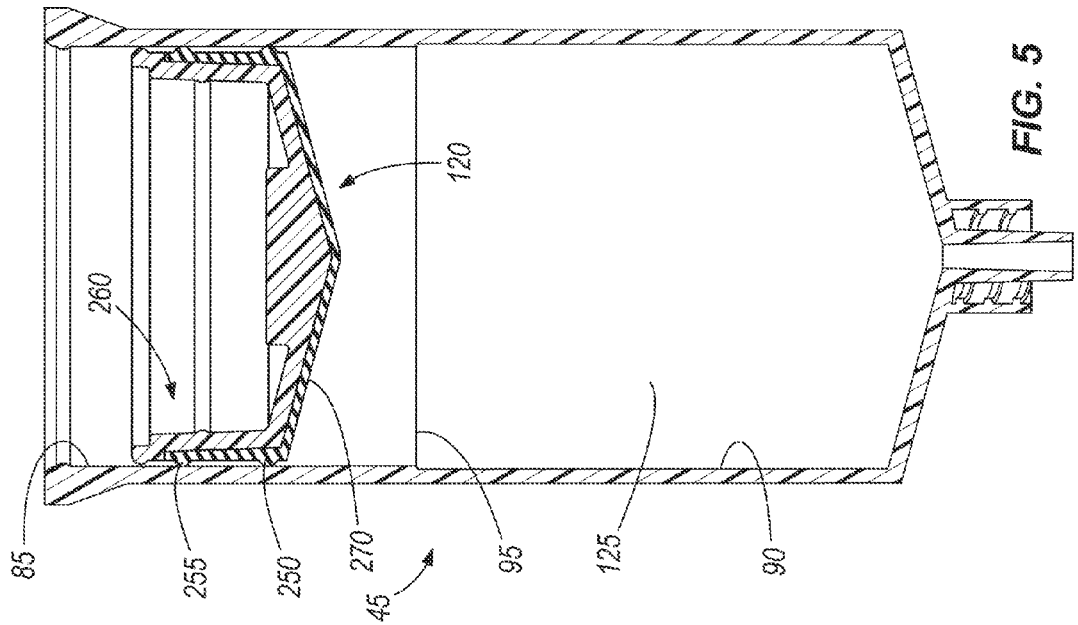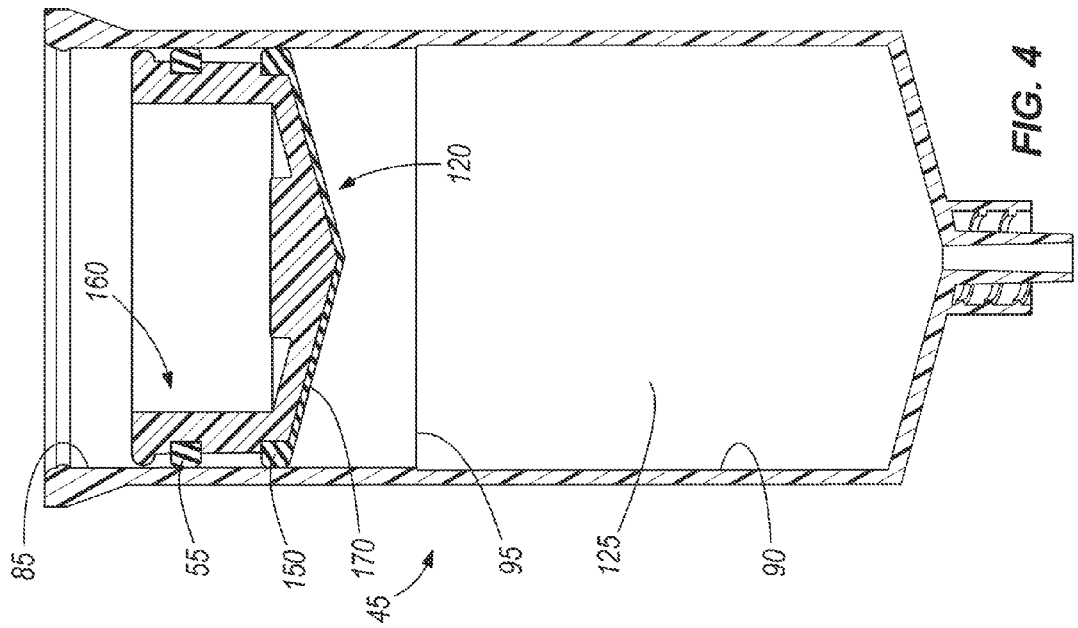

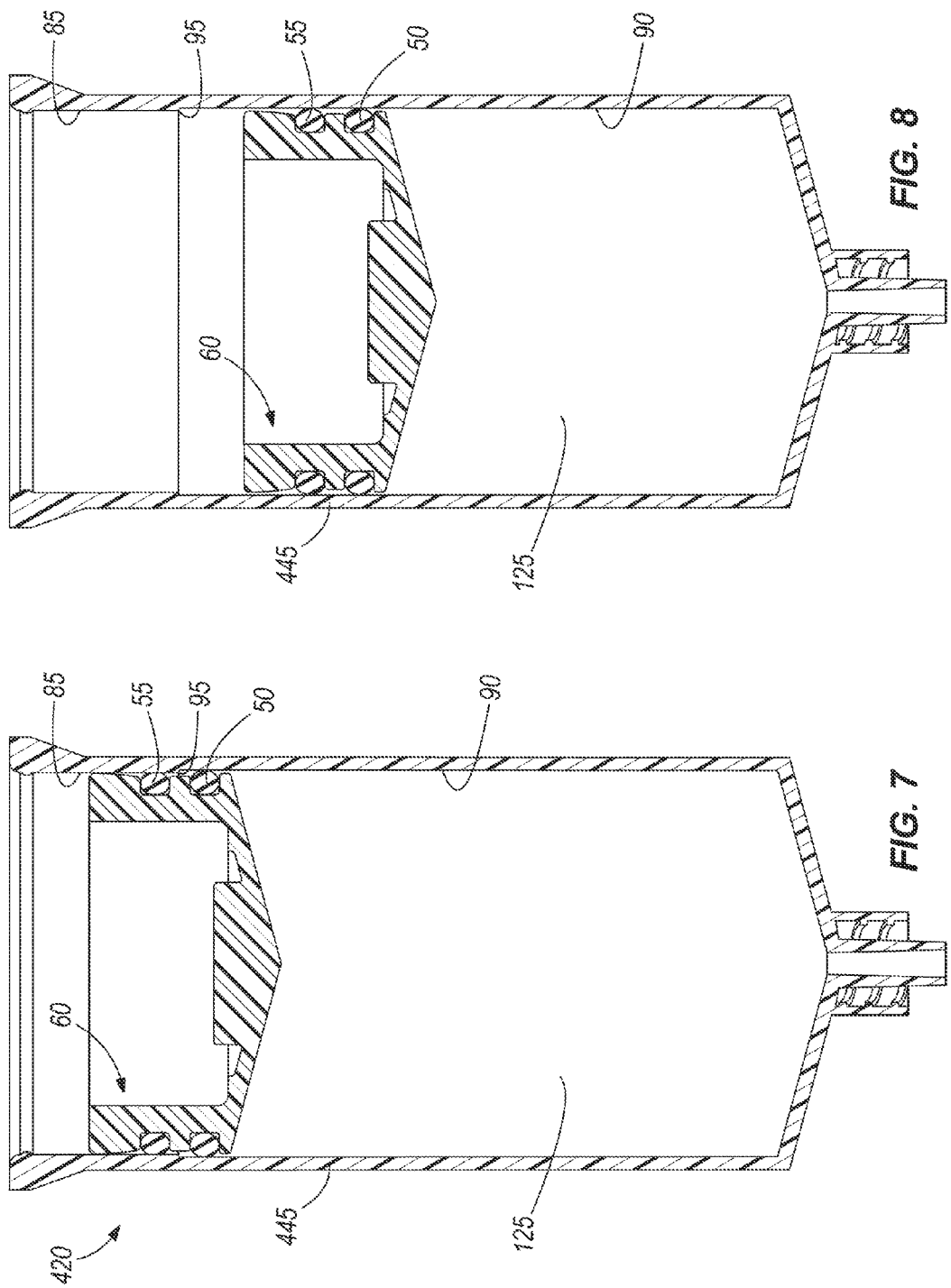

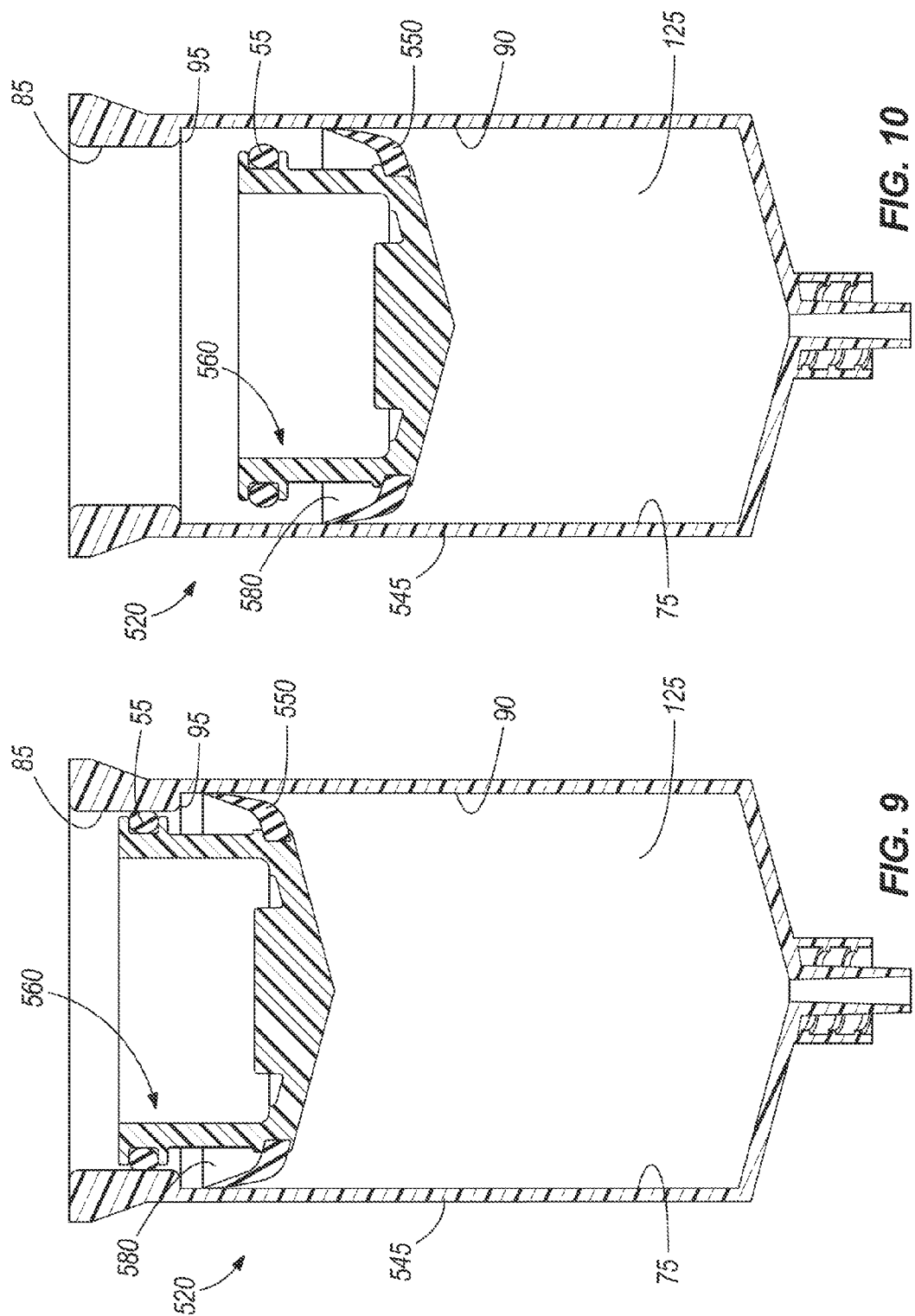

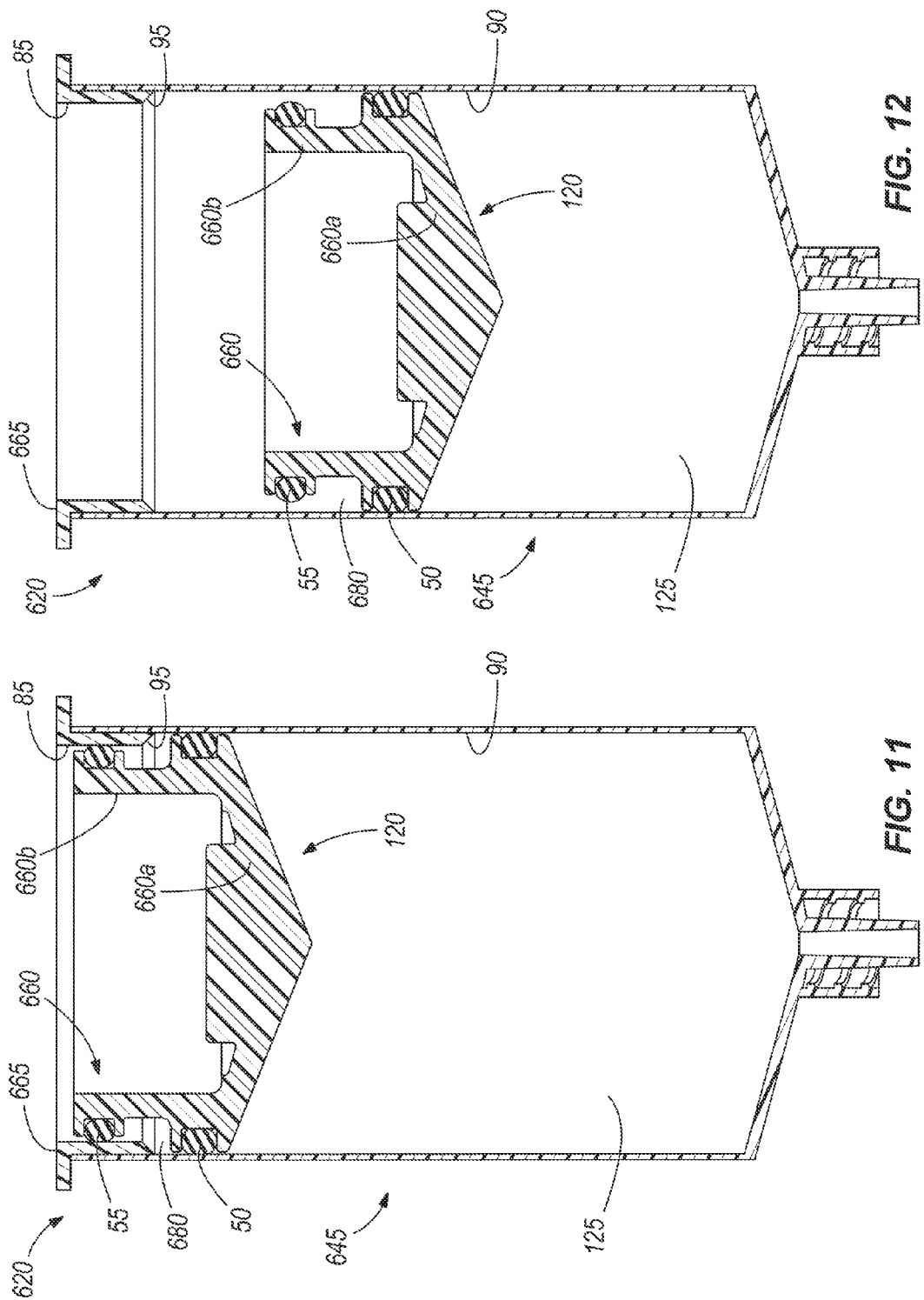

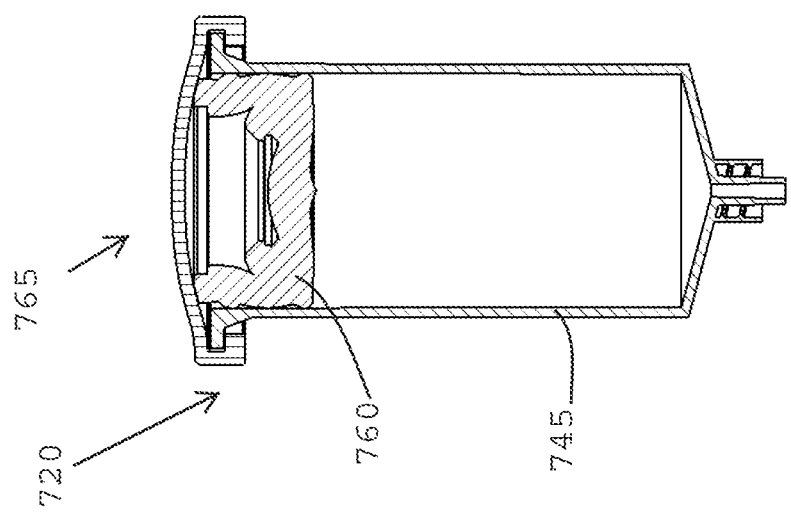
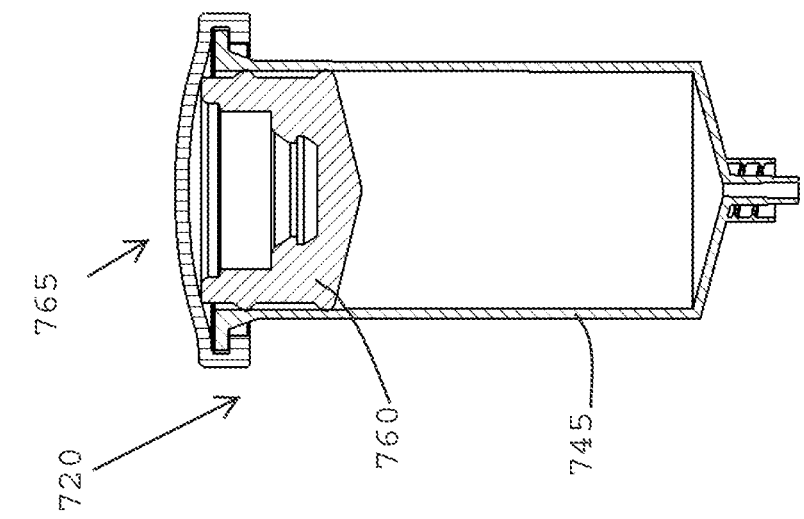
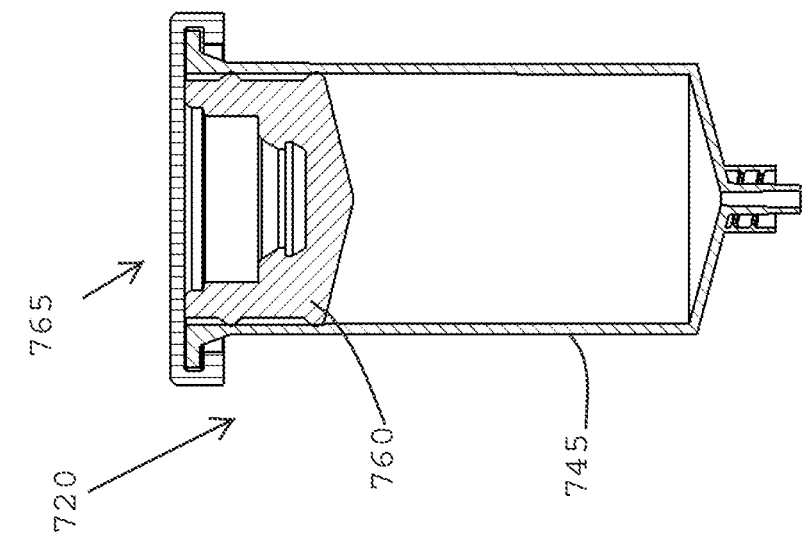

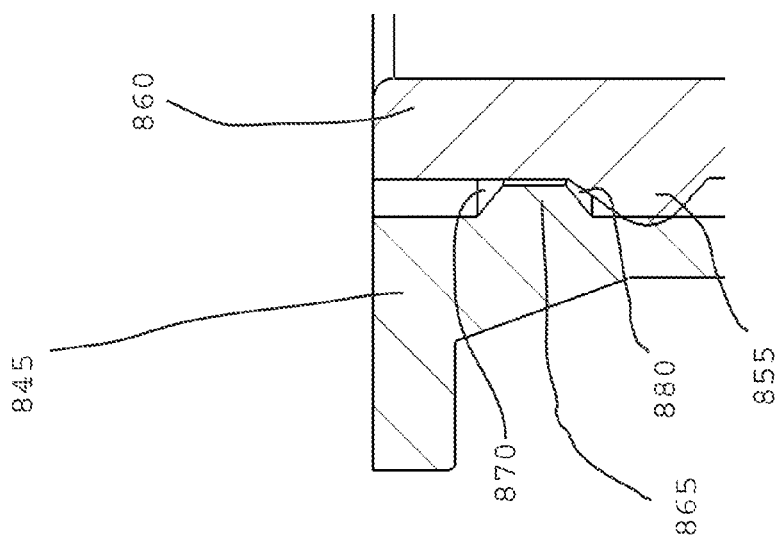
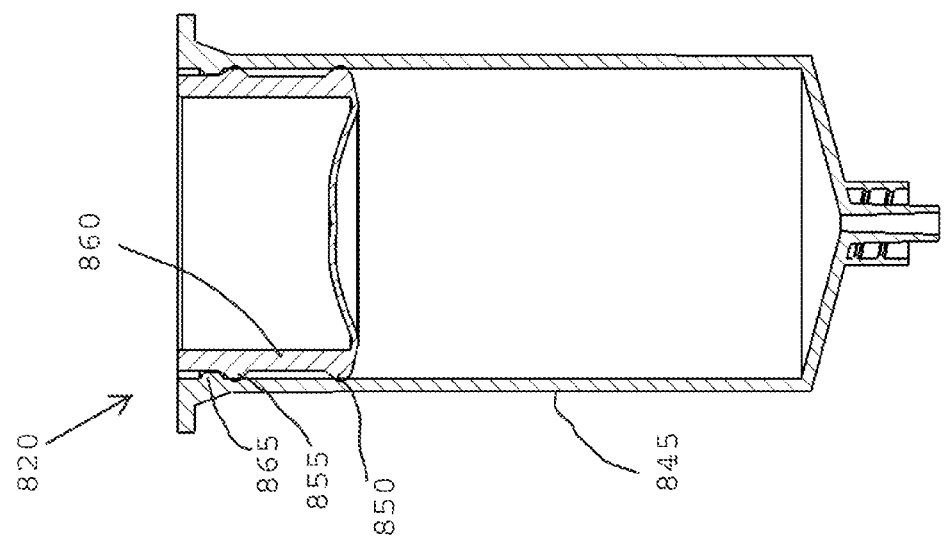
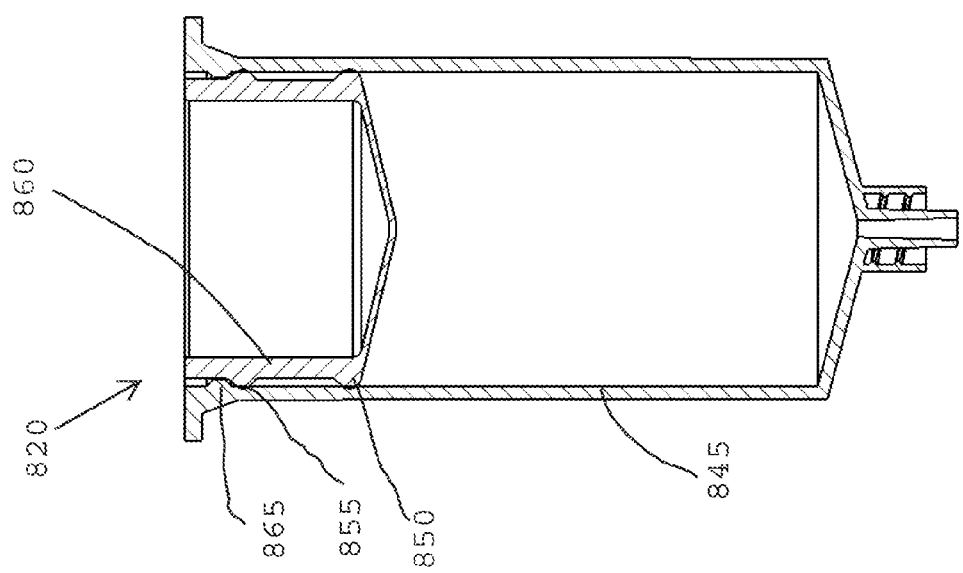

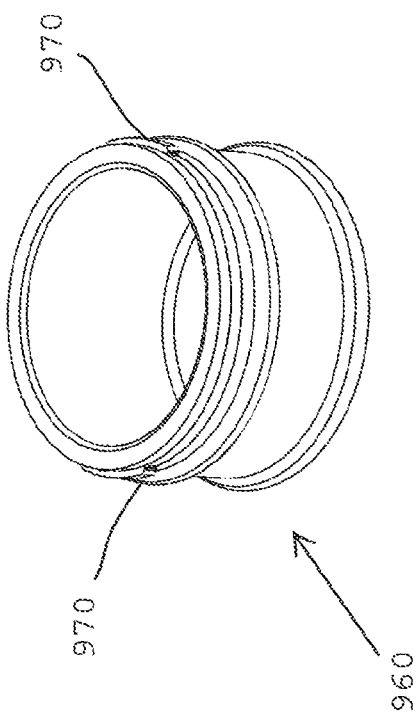
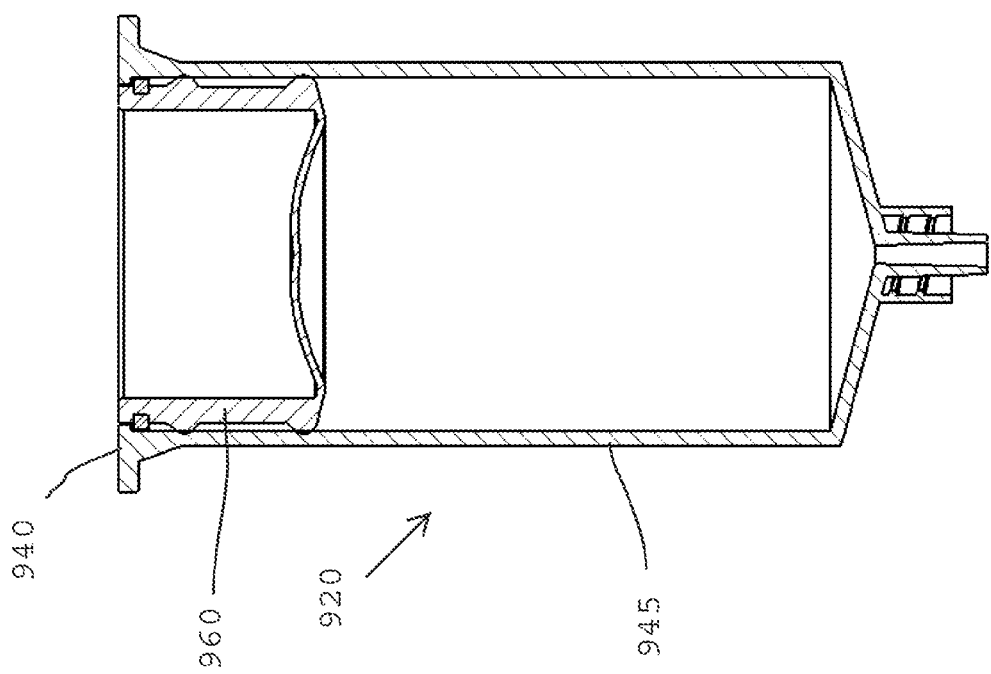

SYRINGE WITH TWO-STAGE SEALING PRESSURE

This application claims priority to U.S. Provisional Application No. 61/763,777 filed Feb. 12, 2013, the entire contents of which being incorporated by reference herein.

BACKGROUND

The present invention relates to a syringe for use in a drug infusion system. The syringe is configured to have a relatively tight seal when full, and a relatively loose seal as product is being dispensed. The relatively tight seal helps maintain a gas-tight seal between plunger and barrel during a freeze and thaw cycle to which the syringe and product is exposed. The relatively loose seal permits the plunger to be pushed down the barrel to dispense product with lower force on the plunger, to reduce power consumption of the pump and extend battery life.

SUMMARY

The invention provides a syringe for use in a drug infusion system, the syringe comprising: a barrel having a cylindrical wall, the cylindrical wall having a first portion with a first inner diameter and a second portion with a second inner diameter that is larger than the first inner diameter; a plunger within the barrel; wherein a sealing member of the plunger engages the first portion of the barrel with a first contact pressure when the barrel is filled with product, such that a first force is required to move the plunger with respect to the barrel; wherein a portion of the plunger engages the second portion of the barrel with a second contact pressure that is lower than the first contact pressure, such that a second force is required to move the plunger in the second portion; and wherein the second force is lower than the first force.

In some embodiments, the first contact pressure gives rise to a seal between the plunger and the first portion of the barrel, which seal is gas-tight through a temperature range of −25° C. to 40° C. In some embodiments, the plunger includes at least one o-ring; and wherein the o-ring gas-tightly seals against the cylindrical wall of the barrel in both of the first and second portions. In some embodiments, the sealing member gas-tightly seals against the first portion of the barrel; and does not gas-tightly seal against the second portion of the barrel. In some embodiments, the plunger includes a plunger head with at least one rim in addition to the sealing member; wherein the sealing member does not engage the second portion of the barrel; and wherein the at least one rim engages the inner surface of the second portion of the barrel. In some embodiments, the first portion of the barrel includes a reduced diameter member inserted into the barrel. In some embodiments, the sealing member of the plunger includes a flexible wiper. In some embodiments, a step is defined between the first and second portions of the barrel; and wherein the sealing member engages the step to resist movement of the plunger in a rearward direction with respect to the barrel.

The invention also provides a method for storing and dispensing a product having a high content of water, the method comprising: providing a syringe barrel having a cylindrical wall, the cylindrical wall having a first portion with a first inner diameter and a second portion with a second inner diameter that is larger than the first inner diameter; providing a plunger having a sealing member; inserting the plunger into the barrel; filling the syringe with product such that the plunger is positioned within the first portion of the barrel; engaging the first portion of the barrel with the sealing member to give rise to a first contact pressure when the barrel is filled with product; applying a first force to overcome the first contact pressure and move the plunger out of the first portion and into the second portion to dispense product; engaging the second portion of the barrel with a portion of the plunger to give rise to a second contact pressure that is lower than the first contact pressure; and applying a second force lower than the first force to overcome the second contact pressure move the plunger in the second portion to continue dispensing product.

In some embodiments, giving rise to the first contact pressure includes creating a gas-tight seal between the plunger and barrel through a temperature range of −25° C. to 40° C. In some embodiments, providing a plunger having a sealing member includes providing a plunger with at least one o-ring as the sealing member; wherein engaging the second portion of the barrel with a portion of the plunger includes engaging the second portion of the barrel with the at least one o-ring; and wherein the o-ring gas-tightly seals against both of the first and second portions. In some embodiments, engaging the first portion of the barrel with the sealing member includes gas-tightly sealing the plunger with respect to the first portion of the barrel with the sealing member; and wherein engaging the second portion of the barrel with a portion of the plunger does not include gas-tightly sealing the plunger with respect to the second portion of the barrel with the sealing member. In some embodiments, providing a plunger having a sealing member includes providing a plunger head having a sealing member and at least one rim; and wherein engaging the second portion of the barrel with a portion of the plunger includes engaging the second portion of the barrel the at least one rim and not with the sealing member. In some embodiments, the method further comprises inserting a reduced diameter member into the barrel to create the first portion of the barrel. In some embodiments, providing a plunger having a sealing member includes providing the plunger having a flexible wiper as the sealing member. In some embodiments, the method further comprises defining a step between the first and second portions of the barrel; and engaging the step with the sealing member to resist movement of the plunger in a rearward direction with respect to the barrel.

The invention also provides method for storing and dispensing a product having water content, the method comprising: providing a syringe barrel having a front end, a rear end, and a cylindrical wall having an inner surface, the rear end being open, and the front end including an orifice; providing a plunger adapted to fit within the syringe barrel with a sliding seal against the inner surface, a product chamber being defined between the inner surface of the barrel and the plunger; filling the product chamber with the product having water content; attaching a restraining element to the syringe; freezing the product-filled syringe such that the water content of the product freezes and expands; restraining displacement of the plunger with the restraining member during expansion of the water content during freezing; storing the frozen product-filled syringe until an approximate time of use; and at the approximate time of use, thawing the frozen product-filled syringe and actuating the plunger to dispense the thawed product from the syringe through the orifice.

In some embodiments, restraining displacement of the plunger includes abutting the restraining element with the plunger; the method further comprising: pressing the plunger against the restraining element with a force in response to expansion of the water content during freezing. In some embodiments, the method further comprises accommodating expansion of the water content during freezing by deflecting the restraining element when the force exceeds a restraining element deflection threshold. In some embodiments, the method further comprises accommodating expansion of the water content during freezing by deflecting the plunger when the force exceeds a plunger deflecting threshold. In some embodiments, attaching a restraining element includes affixing an end cap to the syringe. In some embodiments, providing a syringe barrel includes forming a mounting structure at the rear end, the mounting structure adapted for mounting the syringe to a pump: and wherein attaching the restraining element includes attaching the restraining element to the mounting structure. In some embodiments, attaching a restraining element includes inserting the syringe into a case and affixing a cap to the case; and wherein restraining displacement of the plunger includes abutting the plunger against the cap. In some embodiments, restraining displacement of the plunger includes accommodating expansion of the freezing water content with deflection of at least one of the plunger and restraining element. In some embodiments, the method further comprises permitting displacement of the plunger toward the restraining element during freezing of the product-filled syringe, prior to restraining displacement of the plunger with the restraining element.

BRIEF DESCRIPTION OF THE DRAWINGS

FIG. 2 illustrates a first syringe configuration in a filled condition.

FIG. 3 illustrates the first syringe configuration in a dispensing condition.

FIG. 4 illustrates the first syringe configuration with a first alternative plunger.

FIG. 5 illustrates the first syringe configuration with a second alternative plunger.

FIG. 7 illustrates a second syringe configuration in a filled condition.

FIG. 8 illustrates the second syringe configuration in a dispensing condition.

FIG. 9 illustrates a third syringe configuration in a filled condition.

FIG. 10 illustrates the third syringe configuration in a dispensing condition.

FIG. 11 illustrates a fourth syringe configuration in a filled condition.

FIG. 12 illustrates the fourth syringe configuration in a dispensing condition.

FIG. 19 illustrates the fifth syringe configuration in an initial accommmodation condition.

FIG. 20 illustrates the fifth syringe configuration in an intermediate accommmodation condition.

FIG. 21 illustrates the fifth syringe configuration in a final accommmodation condition.

FIG. 22 illustrates a sixth syringe configuration in an initial condition.

FIG. 23 illustrates the sixth syringe configuration with the plunger in a deflected condition.

FIG. 24 is an enlarged view of the restraining element of the sixth syringe configuration.

FIG. 25 illustrates a seventh syringe configuration with the plunger in a deflected condition.

FIG. 26 is a perspective view of the plunger for the seventh configuration.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
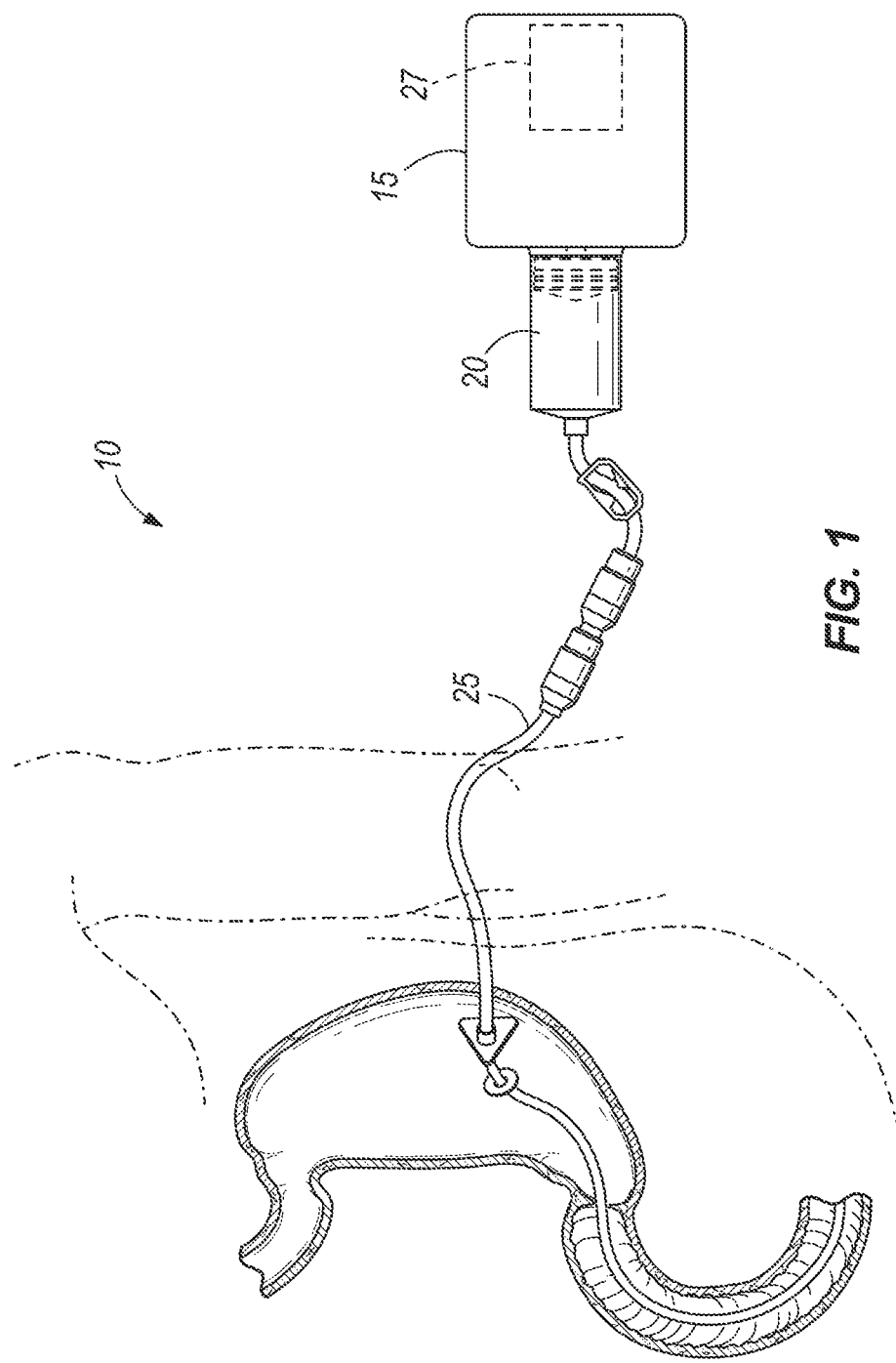
FIG. 1 illustrates an exemplary drug infusion system in which the present invention may be used.

FIG. 1 illustrates a drug infusion system 10 that includes a pump 15, a syringe 20, and a delivery tube 25 that can be inserted into a patient's small intestine. The pump 15 actuates the syringe 20, which displaces product from the syringe 20 into the patient through the tube 25. In many drug infusion systems, the pump 15 actuates the syringe in a slow, steady manner, such that the patient receives the product at an optimal rate over an extended period. The pump can be programmed to deliver the product at a desired rate or according to a desired profile, and the program can be modified in response to the patient's reaction to the product.

The illustrated pump 15 is a portable pump, which can be clipped to a patient's belt or otherwise carried by the patient as the patient moves around. The pump 15 is powered by a portable power source, which may include a single battery, a pack of batteries or another form of portable power. The portable power source will be referred to herein as the battery pack 27 for convenience. In other embodiments, the power source for the pump 15 may be non-portable, such as, for example, a wall outlet and power cord.

An example of a pump that is currently used for drug infusion systems is the Cane Crono pump. Information regarding the Cane Crono pump is available at the company's website www.microjet.it. The Cane Crono pump is cited as merely one example of a pump which can be used in a drug infusion system as contemplated by the present invention. The findings and learnings of the present invention can be applied to drug infusion systems utilizing other pumps; the present invention should not be limited to the specific system illustrated or described. The invention involves advances in syringe design and should not be viewed as limited to the application of a drug infusion system. A drug infusion system is one environment in which such syringe design may be used and is provided here as an example only.

One example of a product administered through a drug infusion system is the Levodopa Carbidopa Intestinal Gel (LCIG) sold under the trademark DUODOPA by Abbott Laboratories. LCIG is used for treating patients with Advanced Parkinson's Disease. As the name implies, LCIG is a gel. The gel is about ninety-six percent (96%) water and therefore behaves much as water behaves during phase changes. Other formulations of LCIG may include a water content of about 94-95%, about 94.58%, or a water content of at least 84%.

LCIG is typically filled into a syringe post-manufacture, and the syringe and its contents are frozen and stored. Depending on its specific composition, the LCIG may have a freezing temperature of about −2° C. (28.4° F.). To ensure the LCIG is solidly frozen, it may be exposed to and stored at temperatures well below the freezing point. The syringes for LCIG product must be gas tight during a two-year storage period and during any shipping of the product. The storage and shipping environment may be maintained, for example, at about negative twenty degrees Celsius (−20° C.) (−4° F.) to ensure the product is solidly frozen.

The syringe 20 must be free from leak paths (i.e., it must be gas tight) during storage, shipping, thawing, and administering. Thawing may be done in a refrigerator at about two degrees Celsius to eight degrees Celsius (2° C. to 8° C.) (35.6° F. to 46.4° F.), for example, prior to being administered to a patient through the drug infusion system. To meet the expected freezing, shipping, thawing, and administering environments, the syringes should accommodate any temperatures and ranges of temperatures between negative twenty-five and forty degrees Celsius (−25° C. to 40° C.) (−13° F. to 104° F.) while maintaining seal integrity (i.e., a gas-tight seal that is free from leak paths). Within this range, the syringes should remain gas tight during a phase change of the gel from liquid to solid and from solid to liquid, which may occur, for example, around −2° C. (28.4° F.). Expected temperature ranges for the syringes include −20° C. to 2° C. (−4° F. to 35.6° F.), −20° C. to 8° C. (−4° F. to 46.4° F.), −20° C. to 40° C. (−4° F. to 104° F.), and −25° C. to 40° C. (−13° F. to 104° F.). The syringes should remain gas tight without regard to the rate of thawing.

Because of the high water content, the product expands as it freezes, and contracts as it thaws. When a filled syringe is placed at −20° C., the gel expands about nine percent (~9%) primarily in the axial direction and pushes the plunger outwards. The stability of the product can be compromised upon mixing with air, the addition of air to the gel may result in a decrease in delivery accuracy of the product to the patient, and there is no provision for the patient or care giver to remove air from the product prior to administration. Consequently, the syringe must accommodate expansion and contraction of the product without permitting air to permeate through the various seals within the syringe.

During the freeze-thaw cycle of a syringe with a conventional, known plunger sealing arrangement, it was observed that: there is a difference in thermal contraction between thermoplastic material, such as polypropylene, and rubber components; there are inadequate dimensions to provide sufficient sealing between the plunger and the syringe barrel over a wide temperature range (−25° C. to 40° C.); and the plunger can tilt/cock/rack during freezing or thawing reducing seal integrity. The result of these conditions leads to ingression of air into the gel during the thaw cycle.

FIGS. 2 and 3 illustrate a first syringe 20 construction. The syringe 20 includes a front end 30 and a rear end 35 and defines a longitudinal axis 40 extending between the front and rear ends 30, 35. Throughout this specification, the terms "front" and "forward" refer to portions, elements, and directions close to or in the direction of the front end 30 of the syringe 20, and the terms "rear" and "rearward" refer to portions, elements, and directions close to or in the direction of the rear end 35 of the syringe 20. The terms "axial" and "axially" mean in a direction parallel to the longitudinal axis 40 of the syringe 20, and the terms "radial" and "radially" mean in a direction perpendicular to the longitudinal axis 40.

The syringe 20 includes a barrel 45, a front o-ring 50, a rear o-ring 55, and a plunger 60 (which may also be referred to as a piston). The barrel 45 is made of thermoplastic material, such as polypropylene. The barrel 45 is generally cylindrical, having an outer surface 70 and an inner surface 75. The inner surface 75 of the barrel 45 defines a barrel diameter 80. The barrel 45 includes a reduced diameter portion 85, an enlarged diameter portion 90, and a step or shoulder 95 between the reduced diameter portion 85 and enlarged diameter portion 90. The step 95 may be longer and at a shallower angle than illustrated. The barrel 45 includes an orifice 100 through which product is dispensed. The orifice 100 communicates with the tube 25.

The front o-ring 50 and rear o-ring 55 surround the plunger 60 and seal between the outside of the plunger 60 and the inner surface 75 of the barrel 45. The rear o-ring 55 prevents or reduces the likelihood of racking. Contact pressure arises between the o-rings 50, 55 and the barrel 45 and between the o-rings 50, 55 and the plunger 60. The contact pressure gives rise to friction. Generally, the higher the contact pressure, the higher the friction. Friction forces while the plunger 60 is at rest can be referred to as static friction and friction forces while the plunger 60 is moving can be referred to as gliding friction.

The seal between the o-rings 50, 55 and the barrel 45 is gas-tight. The phrases "gas-tight," "gas-tightly," and variations of these phrases, when used in reference to a seal in the present disclosure, refer to the seal precluding the movement of air or other gases from one side of the seal to the other side of the seal in the presence of pressure gradients across the seal of a magnitude experienced during thawing of the product within the syringe as discussed herein, which may in some scenarios be on the order of one atmosphere (1 atm), for example.

The plunger 60 is constructed of thermoplastic material, such as polypropylene, and includes a front end having a contact surface 120. A product chamber 125 is defined in the space in the barrel 45 forward of the contact surface 120 and front o-ring 50. The contact surface 120 faces and contacts the product within the barrel 45. The o-rings 50, 55 create a sliding gas-tight seal between the plunger 60 and the barrel 45. The plunger 60 moves axially within the barrel 45 in a forward direction 130 and a rearward direction 135 to decrease and increase, respectively, the volume of the product chamber 125. The plunger 60 maybe said to "advance" when moving in the forward direction 130 and "back up" when moving in the rearward direction 135.

The relative thermal expansion coefficients of the materials from which the barrel 45, plunger 60, and o-rings 50, 55 are made will affect the relative changes in dimensions of the parts during the freeze/thaw cycle. Generally, if the gap between the barrel 45 and plunger 60 increases during freezing, the contact pressure between the o-rings 50, 55 and those components will reduce.

In the case of LCIG, or another product having high water content, freezing the product-filled syringe 20 will cause the product to expand as the water freezes. It will be understood that in all constructions disclosed, a lure cap, well known in the art, is threaded onto the syringe 20 over the orifice 100 so that product cannot escape through the orifice. Expansion of the product-filled syringe 20 will overcome the static friction of the plunger 60 and force the plunger 60 rearward 135, which also expands the volume of the product chamber 125. Expansion of the product may also cause hoop stress in the barrel 45, which radially expands the inner diameter 80 of the barrel 45. The product will take the path of least resistance when expanding, however, so if the static friction of the plunger 60 is low enough, there will be minimal radial or circumferential expansion of the barrel 45 because the product will expand primarily in the axial direction.

The syringe 20 and product will thaw radially inwardly from the outer diameter of the barrel 45. As a consequence, the product will contain an axially-extending column of ice that shrinks in diameter as the product thaws. The column of ice extends from the front end of the barrel 45 to the contact surface 120 of the plunger 60. The column of ice resists movement of the plunger 60 in the forward direction 130, which therefore resists or slows down the shrinking of the volume of the product chamber 125 during thawing. The portion of the product that thaws first (i.e., the radial periphery of the product) will contract before the volume of the product chamber 120 shrinks, which will give rise to pockets or bubbles of vacuum within the thawed portion of the product.

Once thawed, the lure cap can be removed from the front end 30 and the syringe 20 is installed in the pump 15. The pump 15 includes a pushrod or other actuation element that is received in the backside of the plunger 60. The pump 15 applies a linear force on the plunger 60 through the pushrod to linearly displace the plunger 60 in the forward direction 130 within the barrel 45 along the longitudinal axis 40. The pump 15 must first overcome static friction by applying a break-out force to the plunger 60, and then must continually overcome gliding friction by maintain a sufficient gliding force on the plunger 60 to keep the plunger 60 moving in the forward direction 130. As the plunger 60 moves in the forward direction 130, the volume of the product chamber 125 decreases and product is forced out the orifice 100, through the tube 25, and into the patient at a rate prescribed by the physician. The pump 15 draws power from the battery pack 27. The power drawn from the battery pack 27 generally correlates to the force the pump 15 applies to the plunger 60.

The life of the battery pack 27 can be increased if the required glide force is decreased. The syringe construction 20 in FIGS. 2 and 3, and those below attempt to increase the life of the battery pack 27 while providing a tight seal while the syringe is full of product and going through the freezing and thawing cycle. The syringe constructions in this specification provide relatively high contact pressure while the syringe is full, and a lower contact pressure after a predetermined amount of product have been dispensed.

The plunger 60 and o-rings 50, 55 are inserted into the barrel 45. Then the plunger 60 is pulled rearwardly 135 to draw the product into the product chamber 125 through the orifice 100. The plunger 60 and both o-rings 50, 55 are within the reduced diameter portion 85 when the syringe 20 is full. When the syringe 20 is frozen, the product expands, which pushes the plunger 60 rearwardly 135 in the barrel 45. The reduced diameter portion 85 is sufficiently long so that the plunger 60, and more specifically, at least the front o-ring 50, stays within the reduced diameter portion 85 as the plunger 60 backs up in the barrel 45 as the product is frozen.

As discussed above, when it is time to dispense the product, the syringe 20 and its contents are thawed. There is a higher contact pressure on the o-rings 50, 55 arising from the plunger 60 being in the reduced diameter portion 85 during freezing and thawing. The higher contact pressure accommodates the gap between the plunger 60 and barrel 45 increasing during the freezing and thawing cycle, while maintaining a gas-tight seal throughout. This reduces the likelihood that air will be drawn around the o-rings 50, 55 and into the product chamber 125.

Once the product is thawed, the pump 15 pushes on the plunger 60 with the break-out force to overcome the static friction arising from the o-rings 50, 55 sealing against the reduced diameter portion 85. Once the o-rings 50, 55 cross the step 95 and enter the enlarged diameter portion 90, the contact pressure decreases, and the required glide force is reduced so that less power is required to push the plunger 60 forward 130. This conserves energy and increases the life of the battery pack 27.

The shoulder 95 is positioned in the barrel such that the o-rings 50, 55 cross into the enlarged diameter portion 90 when the product chamber has a volume of about 45 mL (i.e., 45 mL of product in the syringe 20). In this example, if the syringe 20 is provided with 50 mL of product when full, the pump must overcome the higher contact pressure of the o-rings 50, 55 in the reduced diameter portion 85 while dispensing the first 5 mL of product. Stated another way, pump 15 only has to overcome the higher contact pressure and sealing forces while dispensing the first 10% of the product, and then overcomes the lower contact pressure and sealing forces while dispensing the remaining 90% of the product.

This arrangement can be said to have a barrel with first and second portions (i.e., the reduced diameter portion 85 and the enlarged diameter portion 90). One or both of the o-rings 50, 55 being a sealing member that engages the first portion with a first contact pressure and that engages the second portion with a second contact pressure that is lower than the first contact pressure. Consequently, a first force is required to break out the plunger from the first portion and a second force, lower than the first force, is required to slide the plunger in the second portion. This two-stage sealing arrangement carries through all constructions and embodiments described in this specification, and provides a relatively tight seal when the syringe is full and the syringe goes through the freezing and thawing cycle through the expected temperature range of −25° C. to 40° C. A relatively loose seal is provided when the plunger is moved within the barrel to dispense product.

Figure 6:
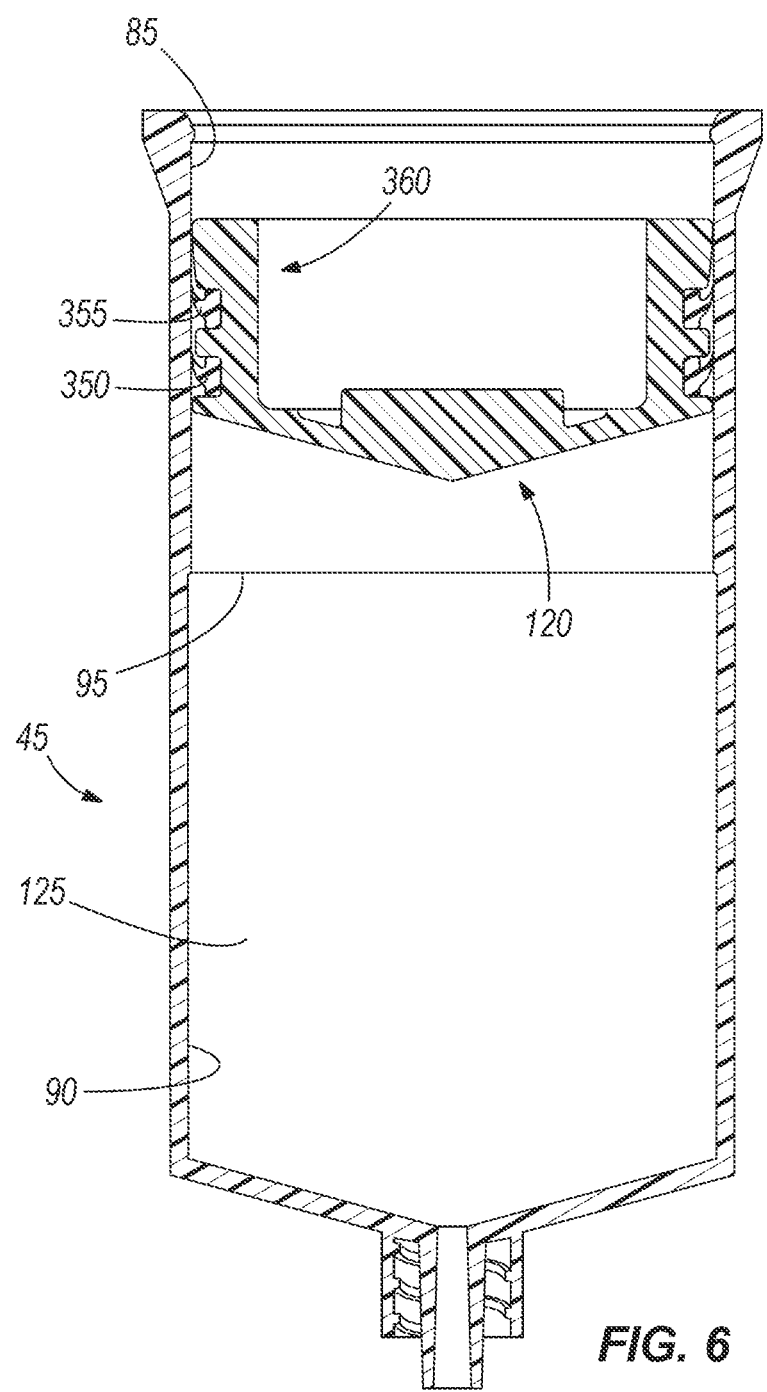
FIG. 6 illustrates the first syringe configuration with a third alternative plunger.
Figure 13:
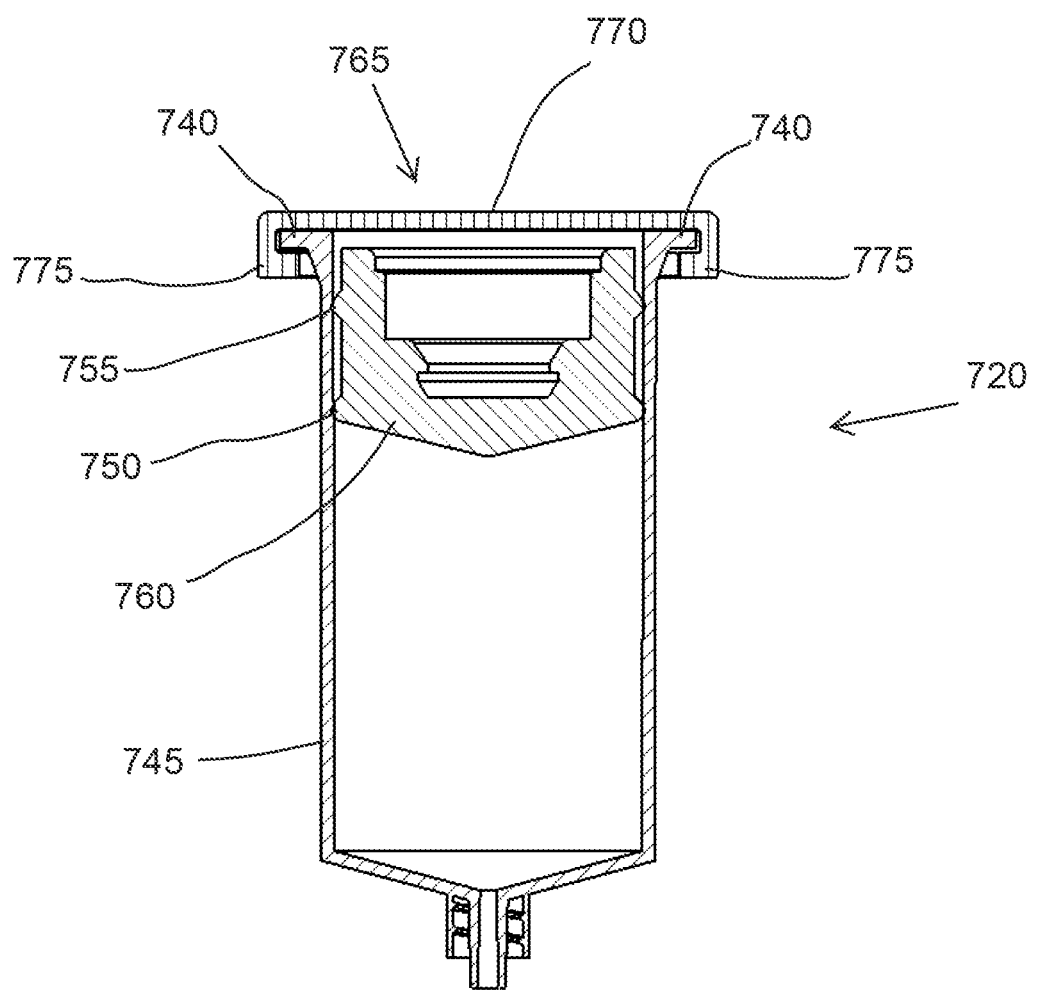
FIG. 13 illustrates a fifth syringe configuration in an initial filled position.

FIGS. 4, 5 and 6 illustrate alternative versions of the plunger for use in the present invention. These alternative versions are provided as examples only, and are not limiting. In FIG. 4, the plunger 160 includes an overmolded seal 170 over the front end of the plunger 160. The overmolded seal 170 provides a sealing rim 150 that performs the same function as the front o-ring 50 of the first plunger 60. The overmolded seal 170 in this construction provides the contact surface 120 and defines a portion of the product chamber 125. The plunger 160 also includes the rear o-ring 55 in this example, to prevent racking.

In FIG. 5, the plunger 260 is covered with an overmolded seal 270 that includes front and rear sealing rims or wipers 250, 255 that perform the same function as the respective front and rear o-rings 50, 55 of the first construction. The overmolded seal 270 defines the contact surface 120 and defines a portion of the product chamber 125.

FIG. 6 illustrates a plunger 360 having wipers 350, 355 in place of the o-rings 50, 55. The wipers 350, 355 resiliently engage and slide against the inner surface of the syringe barrel 45. Because the wipers 350, 355 are swept back (rearward), they may engage or catch on the step 95 in the barrel 45 after they have moved forward of the step 95 and the plunger 360 backs up. For the plunger 360 to back up rearward of the step 95, the wipers 350, 355 will need to double over, fold, or collapse. The wipers 350, 355 will in many configurations provide more resistance to the plunger 360 backing up over the step 95 than the resistance provided by the o-rings 50, 55 and overmolded seals 170, 270. Because of their generally circular or part-circular cross-sections, the o-rings 50, 55 and sealing rims 150, 250, 255 of the overmolded seals 170, 270 include rounded rearward-facing surfaces which will offer some resistance to the plunger 360 backing up over the step 95, but typically not as much resistance as offered by the wipers 350, 355.

It will be understood that plungers 160, 260, 360 are examples of the many different configurations of plungers can be used with the present invention, and that all such variations are contemplated for all syringe constructions disclosed herein. It will be understood that the function of the o-rings 50, 55 of the first exemplary plunger 60 is replaced with the sealing rims or wipers 150, 250, 255, 350, 355 of the other plungers 260, 360, and such sealing rims and wipers can be substituted for the o-rings 50, 55 in the following examples as well, where appropriate. Combinations of the o-rings 50, 55, overmolded seals 170, 270, and wipers 350, 355 can be employed as well. For example, one o-ring 50 or 55 and one wiper 350, 355 can be used in combination on the plunger, or the wiper 355 can be used in place of the rear o-ring 55 with the overmolded seal 170. One of ordinary skill in the art will appreciate all permutations of the various sealing arrangements disclosed herein and apply them to the best advantage in a given syringe arrangement. One of ordinary skill in the art will also factor into the selection of the sealing configuration whether it is desirable to have more or less resistance to the plunger backing up past the step in the barrel or any other rim or lip in the barrel other than the illustrated step.

FIGS. 7 and 8 illustrate a second syringe configuration that includes a syringe 420. The syringe 420 includes a barrel 445, and the above-described front o-ring 50, rear o-ring 55, and plunger 60. The barrel 445 is in all respects the same as barrel 45 described above, except that step 95 is moved rearward. When the syringe 420 is full of product, the front o-ring 50 is forward of the step 95 and the rear o-ring 55 is rearward of the step 95. The rear o-ring 55 is exposed to high contact pressure and provides a tight seal during the freeze-thaw cycle. The syringe 420 is filled with product in the product chamber 125 and frozen, as discussed above. The front o-ring 50 (or any other type of seal used in place of the front o-ring 50) engages the step 95 to resist rearward movement of the plunger 60 as the product is frozen.

Only a relatively small amount of product needs to be dispensed before the rear o-ring 55 crosses the step 95. In one example, if the syringe 420 is full at 50 mL, only about 2 mL needs to be dispensed (i.e., the product chamber 125 is at 48 mL) before the rear o-ring 55 has crossed the step 95. Stated another way, pump 15 only has to overcome the higher contact pressure and sealing forces while dispensing the first 4% of the product, and then overcomes the lower contact pressure and sealing forces while dispensing the remaining 96% of the product. Battery life can be improved with this construction because only a single o-ring 55 gives rise to higher contact pressure and static friction when the syringe 420 is full, and both the front and rear o-rings 50, 55 are within the large diameter portion of the syringe 420 after dispensing relatively little product.

FIGS. 9 and 10 illustrate a third syringe configuration that includes a syringe 520. The syringe 520 includes a barrel 545, a front wiper 550, the rear o-ring 55, and a plunger 560. The barrel 545 is similar to barrel 45 described above in all respects, except that the shoulder 95 is more pronounced and moved rearwardly compared to the barrel 45. The rear o-ring 55 fits tightly between the plunger 560 and the reduced diameter portion 85 to give rise to high contact pressure and air-tight sealing during the freeze-thaw cycle.

The plunger 560 includes a rigid core that is generally cylindrical and of an outer diameter smaller than the reduced diameter portion 85 so that it can move axially through the reduced diameter portion 85. The front wiper 550 is interconnected to the front end of the plunger 560 and contacts the inner surface 75 of the syringe barrel 545 in the enlarged diameter portion 90. The wiper 550 is flexible enough to deflect as the front end of the plunger 560 is pushed through the reduced diameter portion 85 as the plunger 560 is installed in the barrel 545, and then resiliently expand within the enlarged diameter portion 90 to create a seal for the product chamber 125.

The rear o-ring 55 creates an airtight seal between the plunger 560 and the reduced diameter portion 85. The seal between the wiper 550 and the enlarged diameter portion 90 is preferably also air-tight, but it is less critical that this seal be airtight than the rear seal 55. An annular chamber 580 is defined around the plunger 560 between the rear side of the wiper 550 and the rear o-ring 55 when the syringe 520 is filled. The chamber 580 can be evacuated and filled with inert gas when the product chamber 125 is filled with product. Unlike air, the inert gas will not degrade the product in the product chamber 125 if it migrates past the wiper 550.

The syringe 520 is filled with product in the product chamber 125 and frozen, as discussed above. The free edge of the wiper 550 engages the step 95 to resist rearward movement of the plunger 560 as the product is frozen and the plunger 560 attempts to back up.

The seal between the wiper 550 and the inner surface 75 of the barrel 545 may have relatively low contact pressure, such that, as the product is thawed, the inert gas in the chamber 580 may be drawn into the product chamber 125. The wiper 550 creates a seal between the plunger 560 and the barrel 545 sufficient to prevent any substantial volume of product to escape rearwardly around the plunger 560 as the product is dispensed.

As illustrated in FIG. 10, when the plunger 560 has been advanced sufficiently (e.g., 2 mL) to move the rear o-ring 55 across the step 95, the contact pressure between the rear o-ring 55 and the reduced diameter portion 85 drops to zero, and the rear o-ring 55 does not seal against the barrel 545 at all. Once the rear o-ring 55 is disengaged from the reduced diameter portion 85, the only frictional force against the inner surface of the barrel 545 arises from the wiper 550. Once the rear o-ring 55 is disengaged, gliding friction is reduced substantially compared to the static and gliding friction when the syringe 520 is full.

FIGS. 11 and 12 illustrate a fourth construction 620 of the syringe. The syringe 620 includes a barrel 645, the front o-ring 50, the rear o-ring 55, a plunger 660, and an insert 665. The plunger 660 includes a front portion 660*a*, having an enlarged head, and a rear portion 660*b*.

The barrel 645 is generally cylindrical. The insert 665 is inserted into the open rear end of the barrel 645. The barrel 645 and insert 665 define the reduced diameter portion 85 (within the insert 665), the enlarged diameter portion 90 (within the barrel 645), and the step or shoulder 95 defined by the front end of the insert 665 between the reduced diameter portion 85 and enlarged diameter portion 90.

The plunger 660 is inserted into the barrel 645, then the insert 665 is fit within the open rear end of the barrel 645 behind the plunger 660. The insert 665 may be rigidly and permanently affixed to the barrel 645, as by welding or with an adhesive, or may be threaded into the open end of the barrel 645, provided that the interconnect between the insert 665 and the barrel 645 is air tight. Product is drawn into the product chamber 125 by drawing the plunger 660 rearward. The rear o-ring 55 creates an airtight seal between the rear portion 660b of the plunger 660 and the reduced diameter portion 85. The seal between the front a-ring 50 and the enlarged diameter portion 90 is preferably also air-tight, but it is less critical that this seal be airtight than the rear seal 55.

An annular chamber 680 is defined around the plunger 660 between the front and rear o-rings 50, 55 when the syringe 620 is filled. The chamber 665 can be evacuated and filled with inert gas when the product chamber 125 is filled with product. Unlike air, the inert gas will not degrade the product in the product chamber 125 if it migrates past the front o-ring 50.

The syringe 620 is frozen with the product chamber 125 filled with product, as discussed above. The front portion 660a of the plunger 660 engages the step 95 to resist rearward movement of the plunger 660 as the product is frozen and the plunger 660 attempts to back up.

The seal between the front o-ring 50 and the inner surface of the barrel 645 may have relatively low contact pressure, such that, as the product is thawed, the inert gas in the chamber 680 may be drawn into the product chamber 125. The front o-ring 50 creates a seal between the plunger 660 and the barrel 645 sufficient to prevent any substantial volume of product to escape rearwardly around the plunger 660 as the product is dispensed.

As illustrated in FIG. 12, when the plunger 660 has been advanced sufficiently (e.g., 2 mL) to move the rear o-ring 55 across the step 95, the contact pressure between the rear o-ring 55 and the reduced diameter portion 85 drops to zero, and the rear o-ring 55 does not seal against the barrel 645 at all. Once the rear o-ring 55 is disengaged from the reduced diameter portion 85, the only frictional force against the inner surface of the barrel 645 arises from the front o-ring 50. As a result, the rear o-ring 55 is entirely disengaged and gliding friction is reduced substantially compared to the static and gliding friction when the syringe 620 is full.

The above constructions and embodiments provide a method for storing and dispensing a product having a high content of water. In each construction a syringe barrel is provided that has a first portion with a first inner diameter and a second portion with a second inner diameter that is larger than the first inner diameter. A plunger is inserted into the barrel and the syringe is filled with product, such that the plunger is positioned within the first portion of the barrel. A sealing member of the plunger engages the first portion of the barrel to give rise to a first contact pressure when the barrel is filled with product. The sealing member may include first and second sealing members, both of which may be positioned in the first portion of the barrel when the syringe is full, or one of which may be positioned in the first portion and the second of which may be positioned in the second portion of the barrel when the syringe is filled with of product. The first contact pressure is sufficient to maintain a gas-tight seal over the expected temperature ranges −25° C. to 40° C. A first force is applied to the plunger to overcome the first contact pressure and move the plunger out of the first portion and into the second portion to dispense product. The sealing member engages the second portion of the barrel to give rise to a second contact pressure that is lower than the first contact pressure. A second force lower than the first force is sufficient to overcome the second contact pressure and move the plunger in the second portion to continue dispensing product.

FIGS. 13-18 illustrate a fifth construction 720 of the syringe. The syringe 720 includes a barrel 745 and a plunger 760. The barrel 745 includes a pair of radial flanges 740 on the rear end. The radial flanges 740 may be used to mount the syringe 720 into certain types of pumps 15, such as the Cane Crono pump discussed above. Other mounting structure than the radial flanges 740 may be employed, depending on the type of pump 15.

The plunger 760 (which may also be called a piston) is made of resilient rubber, and includes an integral front sealing member 750 and an integral rear sealing member 755. The plunger 760 is a standard, commercially available rubber component.

Figure 14:
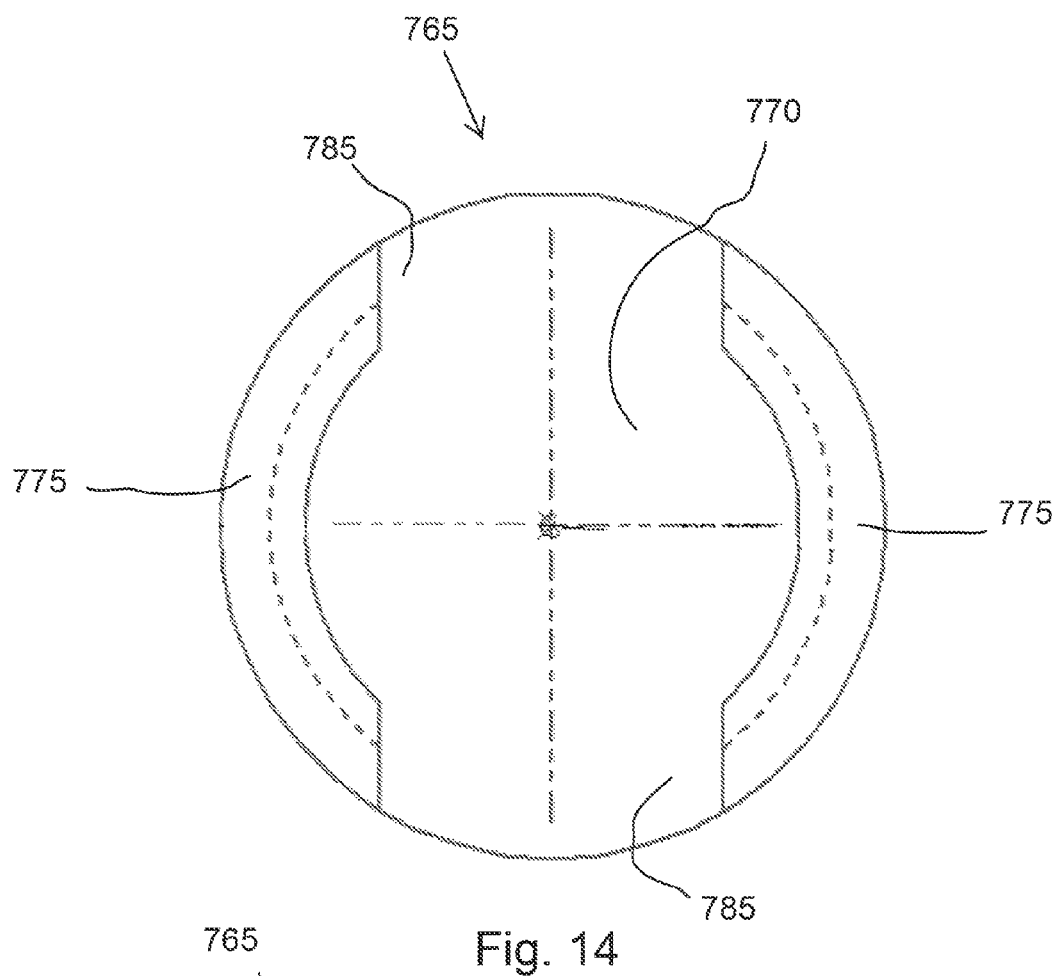
FIG. 14 is a bottom view of an end cap for use with the fifth syringe configuration.
Figure 15:
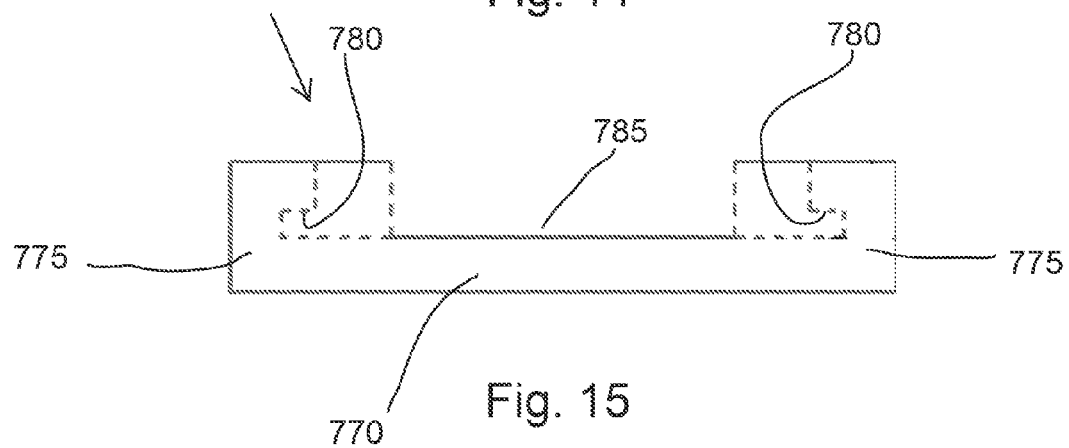
FIG. 15 is a side view of the end cap.

Referring to FIGS. 14 and 15, the assembly further includes an end cap 765. The end cap 765 includes a top 770 and a pair of engaging elements 775. When viewed from the side (FIG. 15), the engaging elements 775 are c-shaped and each defines a channel 780. The engaging elements 775 are diametrically opposed and define between their ends diametrically aligned slots 785 that are wider than the flanges 740 of the syringe 720.

Figure 18:
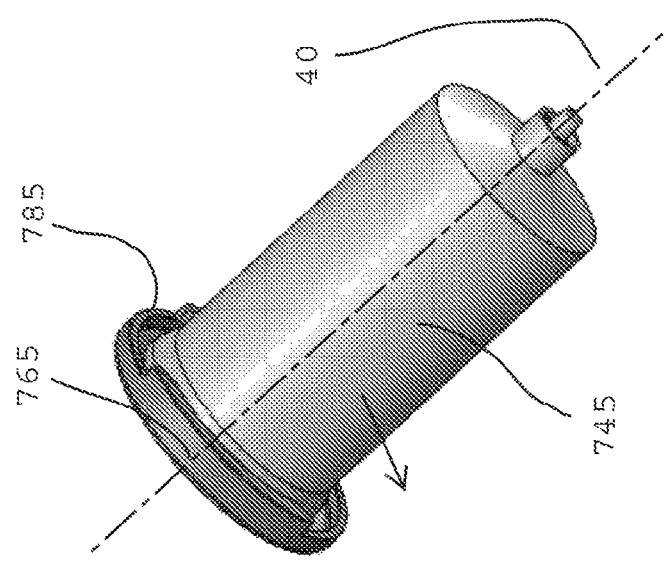
FIG. 18 illustrates a third step for installing the end cap on the syringe.
Figure 17:
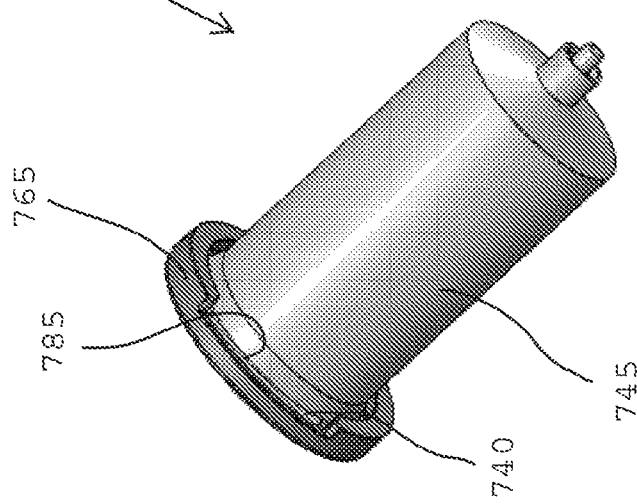
FIG. 17 illustrates a second step for installing the end cap on the syringe.
Figure 16:
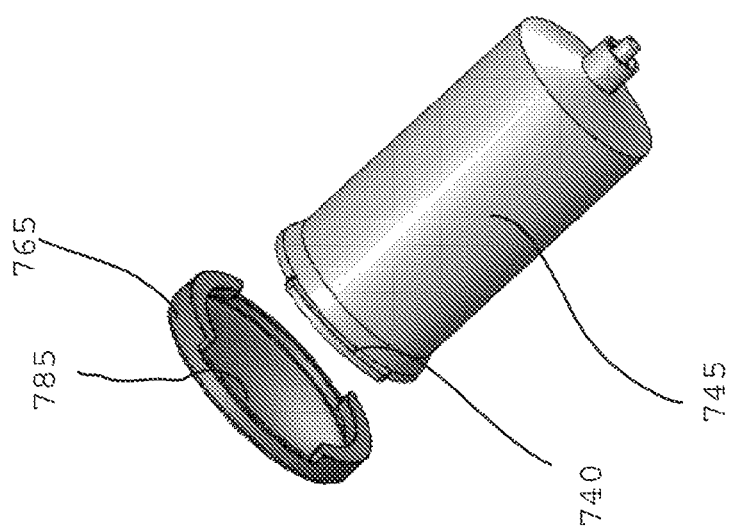
FIG. 16 illustrates a first step for installing the end cap on the syringe.

With reference to FIGS. 16-18, the end cap 765 is installed on the syringe 720 by positioning the flanges 740 in the slots 785 as illustrated in FIGS. 16 and 17, and then rotating the end cap 765 and syringe 720 with respect to each other about the axis 40 so that the flanges 740 slide into the channels 780, as illustrated in FIG. 18. This insert-and-twist assembly process for the end cap 765 is commonly referred to as a bayonet configuration. In other configurations, the end cap 765 is designed to be affixed to whatever mounting structure the syringe includes, which may be the flanges 740 or another structure.

The present invention provides several modes of accommodating the expansion of the product in the syringe as the water content expands during freezing, without compromising at least one of the front and rear seals on the piston and while preventing the piston from racking in the syringe barrel. These modes of accommodation are in addition to slight deflection of the syringe barrel, which may occur, but is not desirable because of the negative affect it may have on the seal between the plunger the barrel.

A first mode of accommodating expansion of the product is illustrated in the sequence of FIGS. 18-19. In FIG. 18, there is space between the plunger 760 and the end cap 765. Expansion of the product pushes or displaces the plunger 760 rearward until the plunger 760 engages the end cap 765. Such displacement is a first mode of accommodating expansion of the product. This first mode of accommodation is also present in all previously-described configurations (FIGS. 2-12).

A second mode of accommodating expansion of the product is illustrated in the sequence of FIGS. 19-20, in which the plunger 760 is pressed against the end cap 765. When force on the end cap 765 exceeds a restraining element deflection threshold, the end cap 765 deflects or bulges. The deflection of the end cap 765 accommodates further expansion of the product.

A third mode of accommodating expansion of the product is illustrated in the sequence of FIGS. 20-21, in which force on the plunger 760 exceeds a plunger deflection threshold. When the force exceeds the plunger deflection threshold, the plunger deflects.

The aspect of the invention directed to accommodating expansion of the product during freezing does not necessarily require all three modes of accommodation, it is possible to configure the syringe assembly to only require any one or two of the three modes. The end cap deflection and plunger deflection may be resilient or non-resilient. In other words, the components may return to their original shape as the load is removed during thawing, or the components may remain deflected. Through design of the components and selection of materials, the restraining element deflection threshold may be higher or lower than the plunger deflection threshold, so it is possible to design the assembly such that the plunger deflects prior to (at a lower force than) the cap.

This second and third modes of accommodation, or either mode, may also be present in all previously-described configurations (FIGS. 2-12) if an end cap or other restraining element is installed on the syringe and if the plunger is designed to deflect. For example, the third mode of accommodating expansion (plunger deflection) may be designed into the configurations of FIGS. 9-10 and 11-12.

In FIGS. 9-10, the wiper 550 may deflect once the plunger deflection threshold is exceeded, a portion of the plunger 560 may deflect, or both the wiper 550 and a portion of the plunger 560 may deflect. In FIGS. 11-12, a portion of the plunger 660 may be designed to deflect upon a plunger deflection threshold being exceeded. As a further analogy between the configurations of FIGS. 9-10, 11-12, and 13-18, the shoulder 95 provided by the syringe barrel 545 in FIGS. 9-10 and by the insert 665 in FIGS. 11-12, and the end cap 765 of FIGS. 13-18 may be broadly referred to as restraining elements, which restrain rearward movement of the plunger at some point.

FIGS. 22-24 illustrate a sixth syringe configuration 820, having a barrel 845 and a plunger 860 similar to the barrel 745 and plunger 760 of the fifth configuration 720 of FIGS. 13-18. The plunger includes a front sealing member 850 and a rear sealing member 855, similar to the front and rear sealing members 750, 755 above. In this configuration, the barrel 845 includes an inwardly extending radial restraining element in the form of a ring 865. As seen in FIG. 24, the ring 865 includes a rear face 870 and forward face 880 that may be slanted. The rear face 870 is slanted or angled such that the front and rear sealing members 850, 855 can slide past the ring 865 with resilient deflection of the plunger 860. The forward face 880 is slanted or angled (or perpendicular to the syringe barrel wall) such that rearward movement of the plunger 760 is arrested and resisted upon the rear sealing member 855 engaging the forward face 880. The ring 865 resists rearward movement of the plunger and forces in excess of the plunger deflection threshold. The head of the plunger 860 will accommodate expansion of product during freezing by deflecting as seen in FIG. 23.

Figure 28:
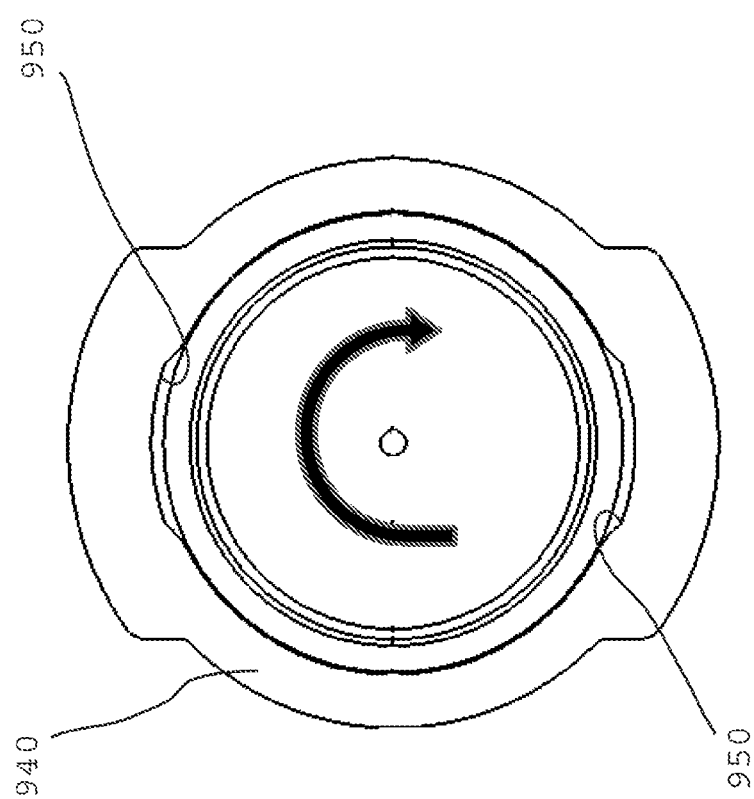
FIG. 28 is rear end view of the syringe barrel of the seventh configuration, with the plunger inserted and rotated.
Figure 27:
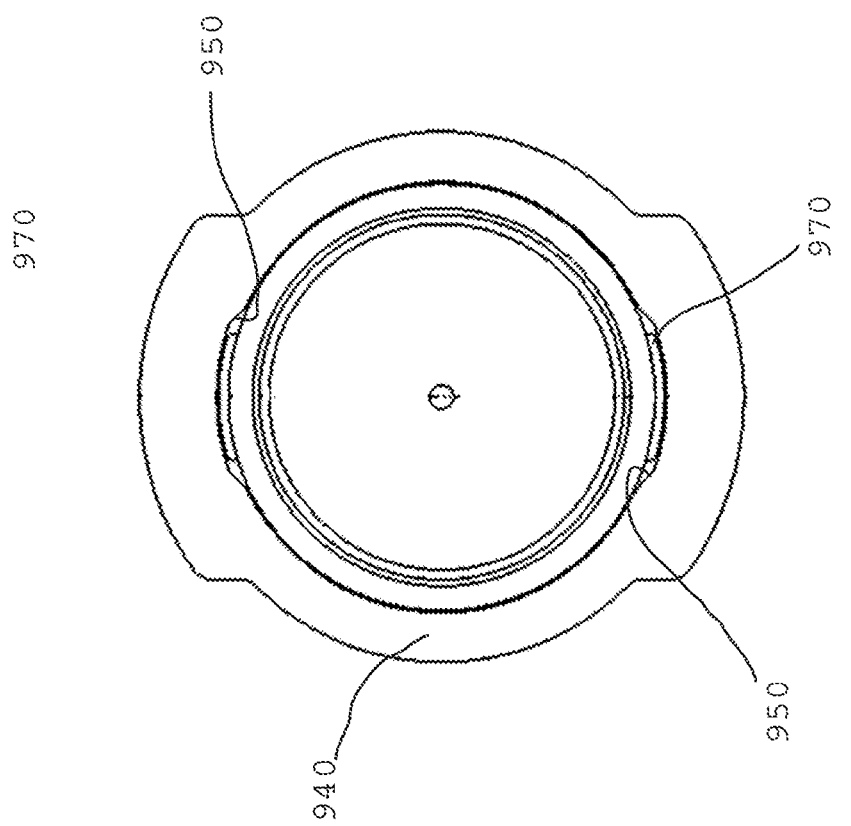
FIG. 27 is a rear end view of the syringe barrel of the seventh configuration, with the plunger inserted.

FIGS. 25-28 illustrates a seventh syringe configuration 920, having a barrel 945 and a plunger 960 similar in many respects to the fifth and sixth configurations described above. The barrel 945 includes a flange 940 at the rear end. The flange 940 overhangs the inner chamber of the syringe barrel 945, with the exception of a pair of diametrically-opposed slots 950 (FIGS. 27, 28). Referring to FIG. 26, the plunger includes a pair of diametrically-opposed lugs 970. The lugs 970 may be integrally molded with the plunger 960 or may be installed after the plunger 960 is molded. In one configuration, the lugs 960 may be integrally formed with a ring that snaps into a circumferential groove around the plunger 960. As illustrated in FIGS. 27 and 28, the plunger 960 fits into the syringe barrel 945 with a bayonet configuration. More specifically, as illustrated in FIG. 27, the lugs 970 of the plunger 960 pass through the slots 950 in the flange 940 as the plunger 960 is inserted into the rear end of the barrel 945. Once the plunger 960 is in the barrel 945, with the lugs 970 having cleared the flange 940, the plunger 960 is rotated about the longitudinal axis 40 as shown in FIG. 28, such that the lugs 970 are under the flange 940. The lug 970 and flange 940 engagement resists rearward movement of the plunger 960 and racking of the plunger 960, and in this regard the flange 940, plunger 960, or both may be called the restraining element in this configuration. In FIG. 25, the plunger 960 is shown in the deflected condition, the plunger 960 and its lugs 970 having been forced against the flange 940 with a force in excess of the plunger deflection threshold.

Figure 29:
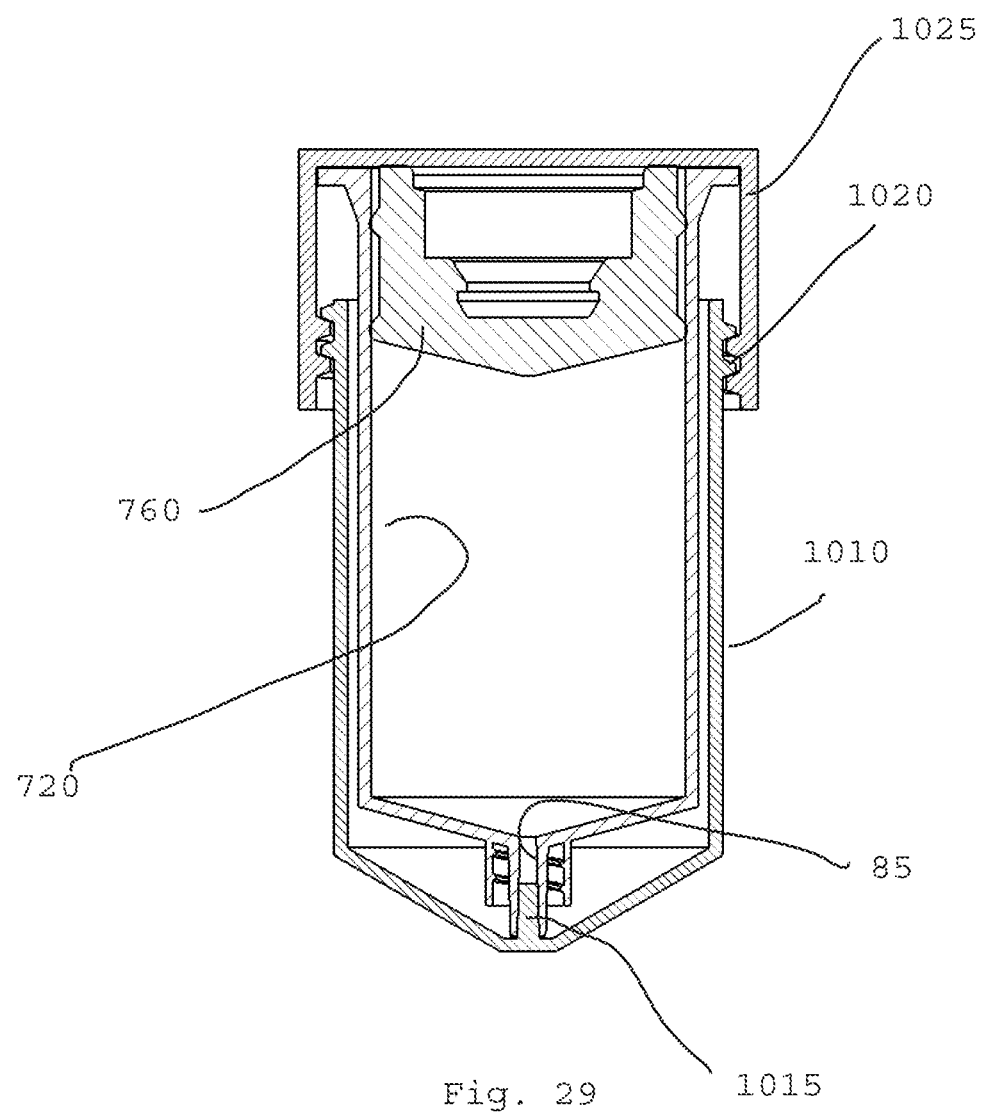
FIG. 29 illustrates an alternative restraining element.

FIG. 29 illustrates an alternative restraining element for a syringe configuration similar to the fifth syringe configuration 720, so the same reference numbers will be used. The alternative restraining element includes a case 1010 into which the syringe 720 is inserted. The bottom of the case 1010 may include a stopper element 1015 that plugs the orifice 85 at the front end of the syringe 720, thereby performing the function of a lure cap. The case 1010 may include male threads 1020 or other connecting mechanism. The restraining element also includes a cap 1025 that interconnects to the case 1010 via the threads 1020 or other connecting mechanism. In this version of the restraining element, the case 1010 and the cap 1025 are dimensioned so that the cap 1025 is held at a desired position (e.g., across the rear end of the syringe 720) to restrain displacement of the plunger 760. As the plunger 760 bears against the cap 1025, the front end of the syringe 720 bears against the bottom of the case 1010. The case 1010 and cap 825 surround the syringe 720 and protect it from light.

Thus, the invention provides, among other things, a gas-tight sealing arrangement for a plunger of a syringe, and a method for storing and dispensing product in such a syringe that includes freezing and thawing the syringe and product while maintaining the gas-tight sealing arrangement throughout the process. The invention also provides methods and apparatus for accommodating expansion of freezing water in the product contained in the syringe. Such methods include rearward displacement of the plunger, deflection of a portion of the plunger, deflection of a restraining element, or a combination of one or more of these methods. The apparatus includes a step in the syringe barrel, an end cap affixed to the rear end of the syringe barrel, a case surrounding the syringe, or another form of restraining element. Various features and advantages of the invention are set forth in the following claims.

What is claimed is:

1. A method for storing and dispensing a product having a high content of water, the method comprising:
    providing a syringe barrel having a cylindrical wall, the cylindrical wall having a first portion with a first inner diameter and a second portion with a second inner diameter that is larger than the first inner diameter;
    providing a plunger having a sealing member;
    inserting the plunger into the barrel;
    adding product to the first portion and the second portion of the syringe barrel such that the plunger is positioned within the first portion of the barrel;
    engaging the first portion of the barrel with the sealing member to give rise to a first contact pressure when the first portion and the second portion include the product;
    applying a first force to overcome the first contact pressure and move the plunger out of the first portion and into the second portion to dispense product;
    engaging the second portion of the barrel with a portion of the plunger to give rise to a second contact pressure that is lower than the first contact pressure; and applying a second force lower than the first force to overcome the second contact pressure to move the plunger in the second portion to continue dispensing product.

2. The method of claim 1, wherein giving rise to the first contact pressure includes creating a gas-tight seal between the plunger and barrel through a temperature range of −25° C. to 40° C.

3. The method of claim 1, wherein providing a plunger having a sealing member includes providing a plunger with at least one o-ring as the sealing member;

wherein engaging the second portion of the barrel with a portion of the plunger includes engaging the second portion of the barrel with the at least one o-ring; and wherein the o-ring gas-tightly seals against both of the first and second portions.

4. The method of claim 1, wherein engaging the first portion of the barrel with the sealing member includes gas-tightly sealing the plunger with respect to the first portion of the barrel with the sealing member; and wherein engaging the second portion of the barrel with a portion of the plunger does not include gas-tightly sealing the plunger with respect to the second portion of the barrel with the sealing member.

5. The method of claim 1, wherein providing a plunger having a sealing member includes providing a plunger head having a sealing member and at least one rim; and wherein engaging the second portion of the barrel with a portion of the plunger includes engaging the second portion of the barrel the at least one rim and not with the sealing member.

6. The method of claim 1, further comprising inserting a reduced diameter member into the barrel to create the first portion of the barrel.

7. The method of claim 1, wherein providing a plunger having a sealing member includes providing the plunger having a flexible member as the sealing member.

8. The method of claim 1, further comprising defining a step between the first and second portions of the barrel; and engaging the step with the sealing member to resist movement of the plunger in a rearward direction with respect to the barrel.

* * * * *

UNITED STATES PATENT AND TRADEMARK OFFICE
CERTIFICATE OF CORRECTION

PATENT NO.        : 9,669,165 B2
APPLICATION NO.   : 13/829251
DATED             : June 6, 2017
INVENTOR(S)       : Mackey et al.

It is certified that error appears in the above-identified patent and that said Letters Patent is hereby corrected as shown below:

In the Claims

Column 16, Line 8, Claim 5: delete "the barrel the at least one rim" and insert --the barrel with the at least one rim--

Signed and Sealed this
Twenty-seventh Day of March, 2018

Andrei Iancu
*Director of the United States Patent and Trademark Office*